United States Patent
Plochocka et al.

(10) Patent No.: US 7,122,602 B2
(45) Date of Patent: *Oct. 17, 2006

(54) PROCESS OF MAKING POLYMERIC HYDROGELS BY REACTIVE EXTRUSION

(75) Inventors: Krystyna Plochocka, Scotch Plains, NJ (US); Timothy G. Bee, North Plainfield, NJ (US)

(73) Assignee: ISP Investments Inc., Wilmington, DE (US)

( * ) Notice: Subject to any disclaimer, the term of this patent is extended or adjusted under 35 U.S.C. 154(b) by 332 days.

This patent is subject to a terminal disclaimer.

(21) Appl. No.: 10/801,232

(22) Filed: Mar. 16, 2004

(65) Prior Publication Data

US 2005/0075454 A1    Apr. 7, 2005

Related U.S. Application Data

(60) Continuation-in-part of application No. 10/397,900, filed on Mar. 26, 2003, now Pat. No. 6,706,817, which is a division of application No. 10/177,995, filed on Jun. 21, 2002, now Pat. No. 6,583,225.

(51) Int. Cl.
*A61K 47/30* (2006.01)
*A61K 47/38* (2006.01)
*C08F 8/28* (2006.01)

(52) U.S. Cl. ................. 525/193; 525/252; 525/253
(58) Field of Classification Search ................ 525/191, 525/193, 252, 253
See application file for complete search history.

(56) References Cited

U.S. PATENT DOCUMENTS 5,635,568 A * 6/1997 Plochocka et al. .......... 525/362
6,583,225 B1 * 6/2003 Plochocka et al. .......... 525/193
6,706,817 B1 * 3/2004 Plochocka et al. .......... 525/193

* cited by examiner

*Primary Examiner*—Nathan M. Nutter
(74) *Attorney, Agent, or Firm*—William J. Davis; Walter Katz

(57) ABSTRACT

What is described is a reactive extrusion process of making a polymeric hydrogel of a polymeric anhydride or acid, e.g. maleic anhydride or maleic acid polymer, or copolymer thereof, crosslinked with a crosslinking agent containing at least 2 crosslinkable groups, particularly, —OH or —NH$_2$, or both. The reaction product is a crosslinked polymeric ester or amide/imide, or both, suitably having a mole ratio of —OH, or —NH$_2$, to —COOH, of 1:10 to 10:1, preferably 2:10 to 7:1. The hydrogel is particularly swellable in water, e.g. >100% in 1 hour in aqueous media; and forms a thin, tacky layer on a substrate, which property is useful in bioadhesive products.

10 Claims, No Drawings

PROCESS OF MAKING POLYMERIC HYDROGELS BY REACTIVE EXTRUSION

CROSS REFERENCE TO RELATED PATENTS AND APPLICATIONS

This patent application is a continuation-in-part of U.S. patent application Ser. No. 10/397,900, filed on Mar. 26, 2003 now U.S. Pat. No. 6,706,817 which is a division of U.S. patent application Ser. No. 10/177,995, filed on Jun. 21, 2002 now U.S. Pat. No. 6,583,225.

BACKGROUND OF THE INVENTION

1. Field of the Invention

This invention relates to hydrogels, and, more particularly, to polymeric hydrogels which are crosslinked polymeric esters or amides/imides, or both, of a polymeric anhydride or acid, or copolymers thereof, which are very swellable in water, and form thin, tacky layers on a substrate, and bioadhesive products thereof.

2. Description of the Prior Art

Hydrogels are polymeric materials which can swell appreciably in water. However, what is described as hydrogels can be viscous polymeric solutions without the swelling characteristic of a true hydrogel. Such hydrogels also are not tacky, a necessary property for making bioadhesive products. See U.S. Pat. Nos. 4,740,365; 4,990,551; 5,135,753; 5,336,501; and 5,846,214. Accordingly, it is desired to provide new and useful polymeric hydrogels having exceptional swelling properties in water, and which are tacky; and bioadhesive products of such hydrogels.

SUMMARY OF THE INVENTION

What is described herein is a reactive extrusion process of making a polymeric hydrogel which is a polymeric anhydride or acid or copolymer thereof, e.g. maleic anhydride or maleic acid polymer, or copolymer thereof, preferably with an alkylvinylether; e.g. methylvinylether or isobutylvinylether; or an olefin, e.g. ethylene, butylenes or isobutylene; crosslinked with a crosslinking agent having at least 2 crosslinkable groups; e.g. an alcohol, —OH, an amine, —NH$_2$, or alcohol-amine groups, e.g. polyols such as polyvinyl alcohol, glycerol, glucose, sorbitol, pentaerithyritol, nonionic surfactants, alginates, starch, cellulose and its derivatives, ethylene glycol, diethylene glycol and ethoxylated/propoxylated derivatives thereof; or a polyamine or ethoxylated amine, e.g. an aminoalcohol, amino acid and the like.

The polymeric hydrogel of the invention preferably has a mole ratio of —OH or —NH$_2$:COOH of 1:10 to 10:1, most preferably 2:10 to 7:1.

The polymeric hydrogel herein is particularly characterized by its exceptional swelling properties and tackiness, which are useful for making bioadhesive products.

The polymeric hydrogels of the invention are made by reacting a maleic anhydride or maleic acid polymer, or copolymer, with a crosslinking agent having at least 2 crosslinkable groups, particularly a polyol or polyamine, or alcohol amine, in water as solvent, in the presence of an esterification or amidation catalyst.

The reaction product is a crosslinked polymeric ester or amide/imide, or both.

Generally the polymer hydrogels of the invention contain a considerable amount of water, usually about 20 wt % or more.

DETAILED DESCRIPTION OF THE INVENTION

The polymeric hydrogel of the invention is made by a crosslinking reaction between an acidic polymer, particularly copolymers of maleic anhydride or maleic acid, or mixtures thereof, and a comonomer, e.g. an alkylvinylether, such as methylvinylether or isobutylvinylether, or olefin, e.g. ethylene, butylenes or isobutylene; with a suitable crosslinking agent, i.e. a compound having at least 2 groups crosslinkable with such copolymers, such as present in polyols, diols, triols, etc. present in compounds such as glycerol, pentaerithyritol, sorbitol, and nonionic surfactants;, in polymers such as polyvinyl alcohol (PVOH), sugars, e.g. glucose, saccarose, alginates, starch, cellulose, and its derivatives; or amines, or aminoalcohols, present and in polyamines, polyaminoalcohols, ethoxylated amines, amino acids, e.g. arginine, glutamine, lysine and gelatine.

The crosslinking reaction produces a crosslinked polymeric ester or amide/imide, or mixed ester-amide/imide. Unexpectedly this reaction suitably is carried out in an aqueous solution or slurry of polymer and crosslinking agent in the presence of an esterification or amidization catalyst, e.g. sulfuric acid, phosphoric acid or toluene sulfonic acid, at about 60–150° C., preferably 80–140° C.

Preferably the hydrogel is formed by a reactive extrusion process.

The polymeric hydrogel obtained has advantageous swelling properties in various solvent media e.g. water, base, salt, buffers, etc. When applied to a substrate, the polymeric hydrogel of the invention forms a thin, tacky layer suitable for use as a bioadhesive. The hydrogels also are useful in oral care, personal care, wound care and drug delivery systems.

The physical properties of the hydrogel, e.g. swelling/tack/solubility/rate of drying/dispersibility in water, and viscoelastic properties, and feel, etc. can be predetermined by the mole ratio of —OH or —NH$_2$:COOH in the hydrogel, as well as the reaction conditions employed, e.g. temperature, catalyst, reaction time, amount of water, etc.

Preferably the mole ratio of —OH or —NH$_2$:COOH in the hydrogel is 1:10 to 10:1, most preferably 2:10 to 7:1.

The process of the invention is carried out in an extruder having a first section in which the reactants are blended and a second section which can be heated to a selected reaction temperature. A suitable extruder for use in the process of the invention is the Werner & Pfleiderer twin screw extruder, e.g. ZSK-30, however other extruders which meet the process requirements of the invention also can be used. The process can be advantageously modified by connecting two extruders in series.

The bioadhesive hydrogels of the invention find wide application in many products, such as topical drug and cosmetic delivery systems; e.g. skin and mucous membranes; personal care products such as skin care; an oral care, e.g. denture liners, flavor and drug delivery; wound care and in systems for drug delivery.

EXAMPLE 1

Into a 14 barrel ZSK-30 twin screw extruder (Werner & Pfleiderer) there are fed two reagents' streams: aqueous solution of 20% wt. poly(vinyl alcohol) (PVOH), containing 20 g/l p-toluenesulfonic acid catalyst and Gantrez® AN 169 BF (methyl vinyl ether/maleic anhydride copolymer, made by ISP) powder. The rate of feeding Gantrez AN 169 BF is such that the weight ratio of PVA/Gantrez is maintained at the desired level, e.g. about 2 in most runs. The components are mixed intimately in the first barrel, which is maintained at 60° to 90° C. The next zone (reaction zone) consists of barrels 2–14, where the temperature is kept at 110° to 50° C. If, however, partial devolatilization of water is desired, the reaction zone consists of barrels 2–9 only, and barrels 10–14 are used for partial evaporation of water and removing trace amount of residual solvent. The devolatilization zone is kept under vacuum at 60° to 100° C. Throughput rates are 10 to 20 lbs/hr.

The material is continuously extruded, through the die, at the surface of moving belt covered with non-woven polyester sheet. Thin tacky layer of semi-transparent, strong, slightly rubbery hydrogel on substrate is obtained. The hydrogel on polyester substrate can be cut into desired shape and can be used for wound care, skin care, drug delivery and similar applications. Other substrates can be used in the process and other continuous shapes can be extruded as well.

Characteristics of the material can be adjusted by varying the following:

Feeding of PVOH solution and Gantrez powder: faster feeding—softer and more tacky material PVOH/Gantrez ratio: more PVOH—more rubbery, less tacky material Devolatilization in the final zone: material having less water, i.e. more rubbery, less tacky Higher temperature in the reaction zone: more rubbery, less tacky material PVOH/Gantrez ratio increasing, % swelling in water decreases

EXAMPLE 2

Using the extruder and parameters as in Example 1 the hydrogel is made by feeding into first barrel aqueous solution containing 100 g/l methyl vinyl ether/maleic acid copolymer (Gantrez® S 97 made by ISP as 12 to 14 wt. % aqueous solution), 250 g/l glycerol and 12.5 g/l sulfuric acid. The product was extruded as above. The material is a transparent, soft, flexible, tacky hydrogel. It is softer and more tacky, and its' degree of swelling in water is higher than that of the material obtained in Example 1. Its properties can be adjusted in a way similar to Example 1.

EXAMPLE 3

Using the extruder and parameters as in Example 2 the hydrogel is made by feeding into first barrel aqueous solution containing 100 g/l methyl vinyl ether/maleic acid copolymer (Gantrez® 97), 68 g/l sorbitol and 12.5 g/l sulfuric acid. The product is extruded as above. Its feel and other characteristics are similar to material made according to Example 2. Its properties can be controlled by adjusting reaction parameters as in Example 1.

While the invention has been described with particular reference to certain embodiments thereof, it will be understood that changes and modifications may be made which are within the skill of the art.

What is claimed is:

1. A process of making a tacky polymeric hydrogel on a substrate comprising maleic anhydride or maleic acid polymer, or copolymer thereof, with an alkylvinylether or olefin, crosslinked with a crosslinking agent having at least 2 crosslinkable groups, where the crosslinkable group is selected from the group consisting of an alcohol (—OH), amine (—NH$_2$) or alcohol-amine (—OH) (—NH$_2$), and water which comprises forming a reaction mixture of maleic anhydride or maleic acid-polymer or copolymer thereof with an alkyl vinyl ether or olefin, with said crosslinking agent, in a predetermined portion as a paste or slurry onto said substrate with water, and reacting and extruding the paste or slurry at a predetermined temperature to form said tacky polymeric hydrogel product.

2. A process according to claim 1 wherein said crosslinking agent is a polyol.

3. A process according to claim 2 wherein said polyol is selected from the group consisting of polyvinyl alcohol, glycerol, glucose, sorbitol, pentaerithyritol, nonionic surfactants, alginates, starch, cellulose.

4. A process according to claim 1 wherein said crosslinking agent is a polyamine or ethoxylated amine.

5. A process according to claim 1 wherein said crosslinking agent is an aminoalcohol.

6. A process according to claim 4 wherein said polyamine is an amino acid.

7. A process according to claim 1 wherein the mole ratio of said alcohol (—OH) or amine (—NH$_2$) groups in the crosslinking agent to carboxyl groups (—COOH) in the polymer or copolymer is 1:10 to 10:1.

8. A process according to claim 7 wherein said mole ratio of —OH or —NH$_2$:COOH is 2:10 to 7:1.

9. A process according to claim 1 wherein water is present in an amount of at least 20% by weight of the hydrogel.

10. A process according to claim 1 in which the crosslinked polymer is an ester or amide/imide, or both.

* * * * *